(12) United States Patent
Takakura et al.

(10) Patent No.: US 8,425,884 B2
(45) Date of Patent: Apr. 23, 2013

(54) O/W EMULSIFIED COMPOSITION

(75) Inventors: Tomiko Takakura, Yokohama (JP); Takafumi Kurosawa, Yokohama (JP)

(73) Assignee: Shiseido Company, Ltd., Chuo-ku, Tokyo (JP)

( * ) Notice: Subject to any disclaimer, the term of this patent is extended or adjusted under 35 U.S.C. 154(b) by 119 days.

(21) Appl. No.: 13/126,176

(22) PCT Filed: Oct. 27, 2009

(86) PCT No.: PCT/JP2009/068395
§ 371 (c)(1),
(2), (4) Date: Apr. 27, 2011

(87) PCT Pub. No.: WO2010/050465
PCT Pub. Date: May 6, 2010

(65) Prior Publication Data
US 2011/0206627 A1  Aug. 25, 2011

(30) Foreign Application Priority Data
Oct. 31, 2008 (JP) ................. 2008-282276

(51) Int. Cl.
*A61K 8/00* (2006.01)
(52) U.S. Cl.
USPC .............................................. 424/59; 424/60
(58) Field of Classification Search .................... None
See application file for complete search history.

(56) References Cited

U.S. PATENT DOCUMENTS

| | | | |
|---|---|---|---|
| 6,899,866 B2 * | 5/2005 | Bonda | 424/59 |
| 8,173,112 B2 | 5/2012 | Ishikubo et al. | |
| 8,182,795 B2 | 5/2012 | Takakura et al. | |
| 2004/0047817 A1 | 3/2004 | Bonda | |
| 2004/0047818 A1 | 3/2004 | Bonda | |
| 2004/0166072 A1 | 8/2004 | Bonda | |
| 2007/0274943 A1 | 11/2007 | Ishikubo et al. | |
| 2009/0028913 A1 | 1/2009 | Takakura | |
| 2010/0209365 A1 * | 8/2010 | Takakura et al. | 424/59 |
| 2010/0233103 A1 | 9/2010 | Shirao et al. | |
| 2010/0247458 A1 | 9/2010 | Kakoki et al. | |

FOREIGN PATENT DOCUMENTS

| | | |
|---|---|---|
| EP | 1920762 A1 | 5/2008 |
| JP | 2005-89366 | 4/2005 |
| JP | 2007-106715 | 4/2007 |
| JP | 2007-204459 | 8/2007 |
| JP | 2007-246521 | 9/2007 |
| JP | 2007-332037 | 12/2007 |
| JP | 2008-100937 | 5/2008 |
| WO | 96/14076 | 5/1996 |
| WO | WO9614076 A1 * | 5/1996 |
| WO | 2005/082325 | 9/2005 |
| WO | 2007/122822 A2 | 11/2007 |

OTHER PUBLICATIONS

Extended European Search Report for corresponding EP 09823575 dated Mar. 16, 2012, four pages.
Patent Abstract and computer translation for JP Publication No. 2007-106715 published Apr. 26, 2007, 29 pages.
Patent Abstract and computer translation for JP Publication No. 2007-332037 published Dec. 27, 2007, 17 pages.
Patent Abstract and computer translation for JP Publication No. 2008-100937 published May 1, 2008, 18 pages.
International Search Report for corresponding PCT/JP2009/068395 mailed Dec. 22, 2009, three pages.

* cited by examiner

*Primary Examiner* — David J Blanchard
*Assistant Examiner* — Daniel F Coughlin
(74) *Attorney, Agent, or Firm* — Rankin, Hill & Clark LLP

(57) ABSTRACT

The present invention provides an O/W emulsified composition excellent in formulation stability, feeling in use, and UV protection ability. The emulsified composition according to the present invention is an O/W emulsified composition, wherein (i) a first oil phase and (ii) a second oil phase are dispersed separately in an aqueous phase,
(i) the first oil phase having average particle size of 700 nm or less, comprising an organic UV absorber, and being formed with, as an emulsifier, a polyoxyethylene/polyoxyalkylene alkyl ether block polymer represented by formula (1) or (2):

$$R_1O-(PO)m-(EO)n-H \qquad (1)$$

wherein $R_1$ is a hydrocarbon group having 16 to 18 carbon atoms; PO is an oxypropylene group, EO is an oxyethylene group, and PO and EO are added to each other in block form; and m and n respectively represent average addition mole number of PO and EO, 70>m>4, 70>n>10, and n>m; and $$R_2O-(AO)p-(EO)q-R_3 \qquad (2)$$

wherein $R_2$ and $R_3$ are either identical to or different from each other, and each of them is a hydrocarbon group having 1 to 4 carbon atoms; AO is an oxyalkylene group having 3 to 4 carbon atoms, EO is an oxyethylene group, and AO and EO are added to each other in block form; and p and q respectively represent average addition mole number of AO and EO, $1 \leq p \leq 70$, $1 \leq q \leq 70$, and $0.2 < (q/(p+q)) < 0.8$, and
(ii) the second oil phase comprising a silicone oil and being formed with, as an emulsifier, an alkyl-modified carboxyvinyl polymer.

8 Claims, No Drawings

O/W EMULSIFIED COMPOSITION

RELATED APPLICATIONS

This application claims the priority of Japanese Patent Application No. 2008-282276 filed on Oct. 31, 2008, which is incorporated herein by reference.

FIELD OF THE INVENTION

The present invention relates to an oil-in-water (O/W) emulsified composition and, in particular, to an O/W emulsified composition which contains an oil-soluble organic UV absorber and a silicone oil, and is excellent in formulation stability as well as feeling in use and suitable as a sunscreen cosmetic.

BACKGROUND OF THE INVENTION

Recently, the effect of ultraviolet on the skin has become widely known recently, and users have become increasingly conscious of skin whitening. Thus, there is demand for a cosmetic which provides a higher UV protection ability and even a good feeling in use.

Due to the fact that an O/W emulsified composition can provide refreshing and light fresh feeling in use while it contains oils, such emulsified composition is widely used not only in cosmetics for basic skin care such as milky lotions and creams, but also in products such as foundations and sunscreen cosmetics.

In cosmetics, UV protection ability has been often provided by incorporating organic UV absorbers or inorganic UV scatterers such as fine particle titanium oxide and fine particle zinc oxide. However, when a high UV protection ability is tried to be provided over a wide range of UVB to UV-A by incorporating a large amount of inorganic UV shielding powder such as fine particle titanium oxide and fine particle zinc oxide, the finish may become whitish, or frictional or powdery feeling may be caused.

In contrast, many organic UV absorbers are generally highly polar oils and do not cause the problems such as the whitish finish and frictional powdery feeling mentioned above. However, they provide stickiness so much to deteriorate the refreshing feeling of O/W emulsified composition when the emulsified composition is applied to skin. In addition, the emulsion stability tends to decrease. For example, though octocrylene and ethylhexyl methoxycinnamate achieve an excellent UV absorption, it has been difficult to obtain an O/W emulsified composition containing them with a high emulsion stability and a good feeling in use.

It is a common technique to incorporate a silicone oil in a cosmetic to decrease the stickiness. However, there has been a problem that the emulsion stability became significantly deteriorated when an O/W emulsified composition was prepared by mixing a highly polar oil such as an organic UV absorber with a silicone oil.

Also, when an oil-soluble solid component was used by being dissolved in an oil phase, there has been a problem that the polarity change of oil phase due to incorporation of a silicone oil causes precipitation of the solid component.

For example, bis-ethylhexyloxyphenol methoxyphenyl triazine is a highly excellent organic UV absorber because of its UV absorbing ability in a wide range of UV-A to UV-B. It is a crystalline solid at ordinary temperature and is generally used for being dissolved in a highly polar oil. However, bis-ethylhexyloxyphenol methoxyphenyl triazine sometimes precipitates owing to the incorporation of a silicone oil. Thus, it has been difficult to incorporate stably bis-ethylhexyloxyphenol methoxyphenyl triazine in an O/W emulsified composition containing a silicone oil.

Patent Literature 1 describes an O/W hair cosmetic containing two oil phases as follows:

(1) an oil phase (hard oil phase) having the average particle size of 0.5 μm or less formed with a nonionic surfactant which is solid at ordinary temperature and has the Krafft point of 40° C. or more; and (2) an oil phase (soft oil phase) having the average particle size of 0.5 to 100 μm formed with a surfactant and/or an alkyl-modified carboxyvinyl polymer.

However, even in such an O/W emulsified composition, it has been difficult to incorporate stably the organic UV absorber as mentioned above and a silicone oil.

PRIOR ART

Patent Literature

Patent Literature 1: Japanese Unexamined Patent Publication No. 2005-89366

DISCLOSURE OF THE INVENTION

Problem to be Solved by the Invention

The present invention has been made in view of the background, and an object of the invention is to provide an O/W emulsified composition containing an oil-soluble organic UV absorber and a silicone oil with excellent in formulation stability as well as non-sticky and refreshing feeling in use. Furthermore, it is to provide the O/W emulsified composition which is also excellent in UV protection ability.

Means to Solve the Problem

To solve the aforementioned problems, the present inventors have diligently studied and found that, by not mixing a silicone oil phase and a highly polar oil phase containing an organic UV absorber, but dispersing them as separate emulsion particles in an aqueous phase with use of a specific component as an emulsifier, and allowing the highly polar oil phase to have a certain emulsion particle size or less, such two kinds of oil phase particles can be stably dispersed in one aqueous phase, and that an O/W emulsified composition with non-sticky and refreshing feeling in use can be obtained even when a large amount of organic UV absorber is incorporated. They also found that, by dissolving a solid component which is poorly soluble in a silicone oil into such a highly polar oil phase, such a component can keep dissolving stably without precipitation over time, thus leading to completion of the present invention.

The present invention provides an O/W emulsified composition wherein the following (i) first oil phase and (ii) second oil phase are dispersed separately in an aqueous phase:

(i) the first oil phase having average particle size of 700 nm or less, comprising an organic UV absorber, and being formed with, as an emulsifier, a polyoxyethylene/polyoxyalkylene alkyl ether block polymer represented by the following formula (1) or (2); and (ii) the second oil phase comprising a silicone oil and being formed with, as an emulsifier, an alkyl-modified carboxyvinyl polymer.

$$R_1O\text{---}(PO)m\text{-}(EO)n\text{-H} \qquad (1)$$

In the formula (1), $R_1$ is a hydrocarbon group having 16 to 18 carbon atoms; PO is an oxypropylene group, EO is an oxyethylene group, and PO and EO are added to each other in block form; and m and n respectively represent average addition mole number of PO and EO, 70>m>4, 70>n>10, and n>m.

$$R_2O\text{-}(AO)p\text{-}(EO)q\text{-}R_3 \quad (2)$$

In the formula (2), $R_2$ and $R_3$ are either identical to or different from each other, and each of them is a hydrocarbon group having 1 to 4 carbon atoms; AO is an oxyalkylene group having 3 to 4 carbon atoms, EO is an oxyethylene group, and AO and EO are added to each other in block form; and p and q respectively represent average addition mole number of AO and EO, $1 \leq p \leq 70$, $1 \leq q \leq 70$, and $0.2 < (q/(p+q)) < 0.8$.

Also, the present invention provides the O/W emulsified composition comprising octocrylene and/or ethylhexyl methoxycinnamate as the organic UV absorber.

Also, the present invention provides the O/W emulsified composition comprising bis-ethylhexyloxyphenol methoxyphenyl triazine as the organic UV absorber.

Also, the present invention provides the O/W emulsified composition, wherein the organic UV absorber is 8% by mass or more in the composition.

Also, the present invention provides the O/W emulsified composition, wherein the polyoxyethylene/polyoxyalkylene alkyl ether block polymer represented by the formula (1) or (2) is 0.3 to 3% by mass in the composition.

Also, the present invention provides a sunscreen cosmetic, consisting of any of the above-mentioned O/W emulsified compositions.

Also, the present invention provides a method for producing any of the above-mentioned O/W emulsified compositions, comprising:

emulsifying an aqueous phase and the first oil phase comprising the organic UV absorber with, as an emulsifier, the polyoxyethylene/polyoxyalkylene alkyl ether block polymer represented by the formula (1) or (2) to prepare an O/W emulsion (first emulsion), wherein the first oil phase with average particle size of 700 nm or less is dispersed in the aqueous phase;

emulsifying, separately from the first emulsion, an aqueous phase and the second oil phase comprising the silicone oil with, as an emulsifier, the alkyl-modified carboxyvinyl polymer to prepare an O/W emulsion (second emulsion), wherein the second oil phase is dispersed in the aqueous phase; and mixing the first and second emulsions to prepare the O/W emulsified composition, wherein the first and second oil phases are separately dispersed in the aqueous phase.

Also, the present invention provides a method for producing any of the above-mentioned O/W emulsified compositions, comprising:

emulsifying an aqueous phase and the first oil phase comprising the organic UV absorber with, as an emulsifier, the polyoxyethylene/polyoxyalkylene alkyl ether block polymer represented by the formula (1) or (2) to prepare an O/W emulsion (first emulsion), wherein the first oil phase with average particle size of 700 nm or less is dispersed in the aqueous phase; and emulsifying an aqueous phase, the second oil phase comprising the silicone oil, and the first emulsion with, as an emulsifier, the alkyl-modified carboxyvinyl polymer to prepare the O/W emulsified composition, wherein the first and second oil phases are separately dispersed in the aqueous phase.

Effect of the Invention

According to the present invention, the O/W emulsified composition excellent in emulsion stability and feeling in use can be obtained by separately dispersing the first oil phase containing an organic UV absorber and the second oil phase containing a silicone oil in the aqueous phase with use of a specific emulsifier, and allowing the first oil phase to have very fine particles. Furthermore, by dissolving a solid component which is poorly soluble in silicone oil in the first oil phase, the solid component can be contained stably in the emulsified composition without precipitation. The emulsified composition can contain a large amount of organic UV absorber and hence is very useful in sunscreen cosmetics and so on.

BEST MODE FOR CARRYING OUT THE INVENTION

Organic UV Absorber

The organic UV absorber contained in the first oil phase can be an oily UV absorber which is generally used in cosmetics.

Examples of preferable organic UV absorbers include ethylhexyl methoxycinnamate, octocrylene, and bis-ethylhexyloxyphenol methoxyphenyl triazine.

The use of octyl methoxycinnamate and octocrylene in combination is preferred because an excellent UV protection ability can be achieved. They can also dissolve bis-ethylhexyloxyphenol methoxyphenyl triazine well. Moreover, the use of octyl methoxycinnamate, octocrylene, and bis-ethylhexyloxyphenol methoxyphenyl triazine in combination is particularly preferred because a higher UV protection ability can be achieved in a wide range of UV-A to UV-B.

Octocrylene (chemical name: 2-ethylhexyl 2-cyano-3,3-diphenylacrylate) is an UV absorber which is in an oil state at ordinary temperature, and commercially available products such as "Uvinul N539" (manufactured by BASF) and "Parsol 340" (manufactured by DSM Nutrition Japan K.K.) can be easily used.

The amount of octocrylene can be suitably set depending on purposes. From a viewpoint of UV protection ability or solubility of solid components, the amount of octocrylene is preferably 1% by mass or more, more preferably 2% by mass or more, and particularly preferably 3% by mass or more, in the O/W emulsified composition of the present invention. On the other hand, when octocrylene is contained excessively, the feeling in use is deteriorated with stickiness and an oily feeling. Thus, the amount is preferably 10% by mass or less, more preferably 8% by mass or less, and particularly preferably 6% by mass or less, in the O/W emulsified composition of the present invention.

Ethylhexyl methoxycinnamate (octyl methoxycinnamate) is an UV absorber which is in an oil state at ordinary temperature, and commercially available products such as "Parsol MCX" (manufactured by DSM Nutrition Japan K.K.) can be easily used.

The amount of ethylhexyl methoxycinnamate can be suitably set depending on purposes. From a viewpoint of UV protection ability or solubility of solid components, the amount of ethylhexyl methoxycinnamate is preferably 1% by mass or more, more preferably 2% by mass or more, and particularly preferably 4% by mass or more, in the O/W emulsified composition of the present invention. On the other hand, when ethylhexyl methoxycinnamate is contained excessively, the feeling in use is deteriorated with stickiness and an oily feeling. Thus, the amount is preferably 7.5% by mass or less, more preferably 7% by mass or less, and particularly preferably 6% by mass or less, in the O/W emulsified composition of the present invention.

Bis-ethylhexyloxyphenol methoxyphenyl triazine (chemical name: 2,4-bis-{(4-(2-ethylhexyloxy)-2-hydroxy)-phenyl}-6-(4-methoxyphenyl)-(1,3,5)-triazine) is an UV absorber which is solid at ordinary temperature, and commercially available products such as "Tinosorb S" (manufactured by Ciba Specialty Chemicals Inc.) can be easily used. In the O/W emulsified composition of the present invention, bis-ethylhexyloxyphenol methoxyphenyl triazine is dissolved in the first oil phase.

The amount of bis-ethylhexyloxyphenol methoxyphenyl triazine can be suitably set depending on purposes. From a viewpoint of UV protection ability and so on, the amount of bis-ethylhexyloxyphenol methoxyphenyl triazine is preferably 0.5% by mass or more, more preferably 1% by mass or more, and particularly preferably 1.5% by mass or more, in the O/W emulsified composition of the present invention. On the other hand, when bis-ethylhexyloxyphenol methoxyphenyl triazine is contained excessively, it makes easier to cause precipitation of crystals over time. Thus, the amount is preferably 5% by mass or less, more preferably 4% by mass or less, and particularly preferably 3% by mass or less, in the O/W emulsified composition of the present invention.

Examples of other organic UV absorbers include triazine UV absorbers such as bis(resorcinyl)triazine; octyl triazone (2,4,6-tris-[4-(2-ethylhexyloxycarbonyl)anilino]-1,3,5-triazine); benzoic acid UV absorbers such as p-aminobenzoic acid (hereinafter abbreviated as "PABA"), PABA monoglycerin ester, N, N-dipropoxy PABA ethyl ester, N, N-diethoxy PABA ethyl ester, N,N-dimethyl PABA butyl ester, and N,N-dimethyl PABA ethyl ester; anthranilic acid UV absorbers such as homomenthyl-N-acetyl anthranilate; salicylic acid UV absorbers such as amyl salicylate, menthyl salicylate, homomenthyl salicylate, octyl salicylate, phenyl salicylate, benzyl salicylate, and p-isopropanol phenyl salicylate; cinnamic acid UV absorbers such as octyl cinnamate, ethyl-4-isopropylcinnamate, methyl-2,5-diisopropylcinnamate, ethyl-2,4-diisopropylcinnamate, methyl-2,4-diisopropylcinnamate, propyl-p-methoxycinnamate, isopropyl-p-methoxycinnamate, isoamyl-p-methoxycinnamate, octyl p-methoxycinnamate (2-ethylhexyl p-methoxycinnamate), 2-ethoxyethyl-p-methoxycinnamate, cyclohexyl-p-methoxycinnamate, ethyl-α-cyano-β-phenylcinnamate, 2-ethylhexyl-α-cyano-β-phenylcinnamate, and glyceryl mono-2-ethylhexanoyl-dipara methoxycinnamate; benzophenone UV absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone; 3-(4'-methylbenzylidene)-d,l-camphor; 3-benzylidene-d,l-camphor; 2-phenyl-5-methyl benzoxazole; 2,2'-hydroxy-5-methylphenyl benzotriazole; 2-(2'-hydroxy-5'-t-octylphenyl)benzotriazole; 2-(2'-hydroxy-5'-methylphenyl)benzotriazole; dibenzaladine; dianisoylmethane; 4-methoxy-4'-t-butyldibenzoylmethane; 5-(3,3-dimethyl-2-norbornylidene)-3-pentane-2-one, methylene bis-benzotriazolyl tetramethylbutylphenol; and 4,4-diarylbutadiene.

The total amount of the organic UV absorbers can be set depending on a desired UV protection ability, and it is preferably 8% by mass or more, more preferably 9% by mass or more, and particularly preferably 10% by mass or more, in the O/W emulsified composition. In the present invention, even when such a large amount of oil-soluble organic UV absorber is incorporated, the O/W emulsified composition excellent in formulation stability and feeling in use can be obtained. Though the upper limit is not restricted in particular, it is usually 30% by mass or less, and preferably 25% by mass or less.

Silicone Oil

Examples of silicone oils contained in the second oil phase include linear polysiloxanes such as dimethylpolysiloxane, methylphenylpolysiloxane, and diphenylpolysiloxane; cyclic polysiloxanes such as octamethylcyclotetrasiloxane, decamethylcyclopentasiloxane, and dodecamethylcyclohexasiloxane; various kinds of modified polysiloxanes such as amino-modified polysiloxanes, polyether-modified polysiloxanes, alkyl-modified polysiloxanes, and fluorine-modified polysiloxanes; silicon resin having three-dimensional network structure; and silicone rubber. Especially, a silicone oil with a low viscosity of 200 mPa·s or less (20° C.) is effective to decrease of stickiness.

The amount of silicone oil can be suitably set depending on intended effects, and it is preferably 0.1 to 15% by mass, preferably 1 to 10% by mass, and more preferably 3 to 7% by mass, in the O/W emulsified composition of the present invention. When the amount is too small, stickiness cannot be decreased. Even when the silicone oil is contained excessively, an enhanced effect that is commensurate with such amount is hardly expected.

O/W Emulsified Composition

The O/W emulsified composition of the present invention is a composition in which the first oil phase containing an organic UV absorber and the second oil phase containing a silicone oil are dispersed separately in an aqueous phase which is a continuous phase of the emulsified composition.

The production method is not limited in particular, and typically the O/W emulsified composition can be obtained by preparing separately an O/W emulsion containing the first oil phase (hereinafter referred to as "first emulsion") and an O/W emulsion containing the second oil phase (hereinafter referred to as "second emulsion"), followed by mixing them. Alternatively, the O/W emulsified composition also can be obtained by preparing the first emulsion, and then emulsifying the second oil phase together with the first emulsion added as a production component of the second emulsion. As far as any problem is not caused in particular, ingredients other than the essential components can be incorporated in each of the oil phases or the aqueous phase depending on their compatibility or affinity.

In the first emulsion, the first oil phase is emulsified to have the average emulsion particle size of 700 nm or less. When the particle size exceeds 700 nm, the formulation stability or feeling in use becomes deteriorated.

Any emulsification method can be used for the first oil phase so far as the oil phase can be emulsified so finely as to be 700 nm or less. The examples include a high-pressure emulsification method and a microemulsification method using a hydrophilic solvent such as a polyhydric alcohol in the presence of a small amount of water (or in the absence of water) (see Japanese Examined Patent Publication No. S57-29213, Japanese Unexamined Patent Publication No. 2006-182724, etc.); however, they are not limited thereto.

As the emulsifier for the first oil phase, one or more polyoxyethylene/polyoxyalkylene alkyl ether block polymers represented by the following formula (1) or (2) are preferably used. With the use of the emulsifier, the O/W emulsified composition in which the first oil phase is finely and stably emulsified can be easily produced. Moreover, even when the first emulsion thus obtained is added to the second emulsion during the production process thereof, it is not destructed and shows a high stability.

$$R_1O—(PO)m\text{-}(EO)n\text{-}H \quad (1)$$

In the formula (1), $R_1$ is a hydrocarbon group having 16 to 18 carbon atoms, and it is preferably a saturated or unsaturated aliphatic hydrocarbon group. The examples include palmityl, stearyl, isostearyl, oleyl, and linolyl groups.

PO is an oxypropylene group, and EO is an oxyethylene group.

In the formula (1), PO and EO must bond to each other in block form. When they bond to each other in random form, the formulation stability cannot be sufficiently achieved. The addition order of propylene oxide and ethylene oxide is not particularly specified. The block includes not only two-stepwise block, but also three- or more-stepwise block.

m and n respectively represent the average addition mole number of PO and EO, $70>m>4$, $70>n>10$, and $n>m$.

The molecular weight of the block polymer in the formula (1) is preferably 800 or more, and more preferably 1500 or more. When the molecular weight is less than 800, the effect is low. Though the upper limit of the molecular weight cannot be specified particularly, stickiness tends to be caused as the molecular weight becomes larger.

Examples of the block polymer represented by the formula (1) include Nikkol PBC44 (manufactured by Nikko Chemicals Co., Ltd.)

$$R_2O\text{-}(AO)p\text{-}(EO)q\text{-}R_3 \quad (2)$$

In the formula (2), $R_2$ and $R_3$ are either identical to or different from each other, and each of them is a hydrocarbon group having 1 to 4 carbon atoms and preferably a saturated aliphatic hydrocarbon group. The examples include methyl, ethyl, propyl, isopropyl, butyl, isobutyl, sec-butyl, and tert-butyl groups, and more preferably methyl and ethyl groups.

AO is an oxyalkylene group having 3 to 4 carbon atoms, and the examples include oxypropyl and oxybutyl groups. EO is an oxyethylene group.

In the formula (2), AO and EO bond to each other in block form. When they bond to each other in random form, the formulation stability cannot be sufficiently achieved. The addition order of ethylene oxide and alkylene oxide is not particularly specified. The block includes not only two-stepwise block, but also three- or more-stepwise block.

p and q respectively represent the average addition mole number of AO and EO, $1 \leq p \leq 70$, and $1 \leq q \leq 70$, $0.2<(q/(p+q))<0.8$.

The molecular weight of the block polymer in the formula (2) is preferably 1000 or more, and more preferably 3000 or more. When the molecular weight is less than 1000, the effect is low. Though the upper limit of the molecular weight cannot be specified particularly, stickiness tends to be caused as the molecular weight becomes larger.

The block polymer of the formula (2) can be produced in a known method. For example, after addition polymerization of an ethylene oxide and an alkylene oxide having 3 to 4 carbon atoms with a compound having a hydroxyl group, etherification with an alkyl halide is carried out in the presence of an alkaline catalyst, to obtain the product (see Japanese Unexamined Patent Publication No. 2004-83541, etc.).

Specific examples of the block polymer of the formula (2) include POE (14) POP (7) dimethyl ether, POE (10) POP (10) dimethyl ether, POE (7) POP (12) dimethyl ether, POE (15) POP (5) dimethyl ether, POE (25) POP (25) dimethyl ether, POE (27) POP (14) dimethyl ether, POE (55) POP (28) dimethyl ether, POE (22) POP (40) dimethyl ether, POE (35) POP (40) dimethyl ether, POE (50) POP (40) dimethyl ether, POE (36) POP (41) dimethyl ether, POE (55) POP (30) dimethyl ether, POE (30) POP (34) dimethyl ether, POE (25) POP (30) dimethyl ether, POE (14) POB (7) dimethyl ether, POE (10) POP (10) diethyl ether, POE (10) POP (10) dipropyl ether, and POE (10) POP (10) dibutyl ether.

POE, POP, and POB respectively stand for polyoxyethylene, polyoxypropylene, or polyoxybutylene. Hereinafter they may be referred to with these abbreviations.

As even a small amount of these block polymers can emulsify finely and stably the first oil phase, the stable O/W emulsified composition without stickiness owing to surfactants can be obtained. However, when the amount of block polymer is too small, the stable O/W emulsified composition cannot be obtained. Thus, the amount is preferably 0.3 to 3% by mass, more preferably 0.3 to 2% by mass, and particularly preferably 0.3 to 1% by mass, in the composition.

In the second emulsion, the average emulsion particle size of the second oil phase is not particularly limited, and it is normally 0.5 to 15 μm. Even when the emulsion particle is finer than the above, any special effect cannot be achieved. When it is larger than the above, there may be a concern for decreased formulation stability.

The emulsification method of the second oil phase is not particularly limited. An alkyl-modified carboxyvinyl polymer is preferably used as an emulsifier for the second oil phase. The alkyl-modified carboxyvinyl polymer is a water-soluble copolymer of (metha)acrylic acid and $C_{10-30}$-alkyl (metha)acrylate. Furthermore, the alkyl-modified carboxyvinyl polymer may have a crosslinked structure by an appropriate and known polyfunctional ethylenically-unsaturated monomer. The average molecular weight of the copolymer is preferably about 50,000 to 3,000,000.

Examples of preferable alkyl-modified carboxyvinyl polymers include the one represented by the following formula (3):

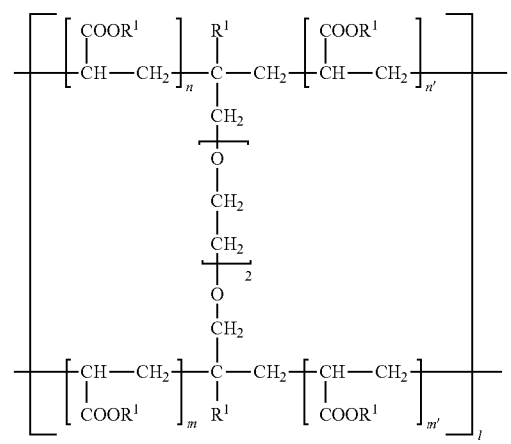

In the formula (3), $R^1$s are respectively alkyl groups having 10 to 30 carbon atoms, and a part of Rs may be hydrogen atoms; n, n', m, and m' respectively represent any integer so that the sum represented by n+n'+m+m' is within the range of 40 to 100; and l represents any integer so that the molecular weight is in a specified range.

Examples of alkyl-modified carboxyvinyl polymers include Carbopol 1342, Pemulen TR-1, and Pemulen TR-2, which are manufactured by B.F. Goodrich Chemical.

The amount of alkyl-modified polymer is preferably 0.01 to 2% by mass, and more preferably 0.05 to 1% by mass, in the composition.

In the O/W emulsified composition of the present invention, other ingredients which can be incorporated in cosmetics can be further contained in addition to the essential components mentioned above so far as the effect of the present invention is not affected. For examples, powders, liquid oils, solid oils, waxes, hydrocarbons, higher fatty acids, higher alcohols, esters, silicones, anionic surfactants, cationic surfactants, amphoteric surfactants, nonionic surfactants, moisturizers, water-soluble polymers, thickeners, film-forming agents, UV absorbers, UV scatterers, metal ion sequestering agents, lower alcohols, polyhydric alcohols, saccharides, amino acids, organic amines, polymer emulsions, pH adjusters, skin nutrients, vitamins, antioxidants, antioxidant aids, perfumes, and water can be suitably incorporated as necessary. When oil components are incorporated, they can be contained in the first oil phase and/or the second oil phase considering the compatibility and so on.

The O/W emulsified composition of the preset invention is applicable in various cosmetics in which sunscreen function is desired. For example, it is applicable in makeup cosmetics such as foundations and lipsticks, as well as milky lotions, creams, and pre-makeup.

EXAMPLES

Hereinafter, the present invention will be further explained with reference to specific examples. However, the present invention is not limited by these examples. The amount is expressed in mass % unless otherwise specified. The evaluation methods used in the present invention are as follows.

(Average Emulsion Particle Size)

The particle size distribution of the first oil phase emulsion (first emulsion) just after preparation was measured with Zetasizer Nano ZS (manufactured by Sysmex Corporation).

(Feeling in Use)

In 20 female panelists, each test sample just after preparation was applied to the face by hand and evaluated according to the following criteria with the questionnaire for stickiness during application and just after application on skin.

O: 16 or more of panelists answered that there was no stickiness.
Δ: 6 or more to 15 or less of panelists answered that there was no stickiness.
X: 5 or less of panelists answered that there was no stickiness.

(Emulsion Stability)

The appearance of each test sample which had been preserved at 50° C. for one month was observed by the naked eye and evaluated according to the following criteria.
O: There is no oil floatation or creaming.
Δ: There are slight oil floatation and creaming.
X: There are oil floatation and creaming.

(Solubility Stability)

The precipitate in each test sample which had been preserved at 0° C. for one month was observed by the naked eye and evaluated according to the following criteria.
O: Crystals or insoluble matter did not precipitate.
Δ: Crystals and insoluble matter precipitated slightly.
X: Crystals and insoluble matter precipitated.

(UV Protection Ability)

The UV protection ability of each test sample just after preparation was measured with in vitro SPECTRO PHOTOMETER U-4100 (manufactured by Hitachi, Ltd.) and evaluated according to the following criteria.
⊚: The absorbance at 310 nm was higher than that of a reference sample showing in vivo measurement value of SPF 30.
O: The absorbance at 310 nm was higher than that of a reference sample showing in vivo measurement value of SPF 16.
X: The absorbance at 310 nm was lower than that of a reference sample showing in vivo measurement value of SPF 16.

Example 1

State of Existing Oil Phase

O/W emulsified compositions were prepared using the compositions in Table 1 according to the following production method.

TABLE 1

| No. | Components | Test Ex. 1-1 | Test Ex. 1-a | Test Ex. 1-b | Test Ex. 1-c | Test Ex. 1-d |
|---|---|---|---|---|---|---|
| 1 | Water | Balance | Balance | Balance | Balance | Balance |
| 2 | Ethanol | 6 | 6 | 6 | 6 | 6 |
| 3 | Octocrylene | 5 | 5 | 5 | 5 | 5 |
| 4 | Ethylhexyl methoxycinnamate | 5 | 5 | 5 | 5 | 5 |
| 5 | Bis-ethylhexyloxyphenol methoxyphenyl triazine | 2 | 2 | 2 | 2 | 2 |
| 6 | Dipropylene glycol | 3 | 3 | 3 | 3 | 3 |
| 7 | Glycerin | 1 | 1 | 1 | 1 | 1 |
| 8 | POE(20)POP(8)cetyl ether | 0.4 | 0.4 | 0.4 | 0.4 | 0.4 |
| 9 | Isostearic acid | 0.2 | 0.2 | 0.2 | 0.2 | 0.2 |
| 10 | Carbomer K | 0.13 | 0.13 | 0.13 | 0.13 | 0.13 |
| 11 | Dimethylpolysiloxane *1 | 3.9 | 3.9 | 3.9 | 3.9 | — |
| 12 | Aminopropyl dimethicone *2 | 0.1 | 0.1 | 0.1 | 0.1 | — |
| 13 | (Acrylic acid/(C10-30)alkyl acrylate) copolymer *3 | 0.07 | 0.07 | 0.07 | 0.07 | 0.07 |
| 14 | Trisodium edetate | 0.02 | 0.02 | 0.02 | 0.02 | 0.02 |
| 15 | BHT | 0.004 | 0.004 | 0.004 | 0.004 | 0.004 |
| 16 | Phenoxyethanol | 0.3 | 0.3 | 0.3 | 0.3 | 0.3 |
| 17 | Methyl paraben | 0.15 | 0.15 | 0.15 | 0.15 | 0.15 |
|  | Production method | Production method 1 or 1' (emulsifying separately) | Production method 2 (emulsifying at once) | Production method 3 (emulsifying separately) | Production method 4 (emulsifying at once) | Production method 1 or 1' (emulsifying separately) |

TABLE 1-continued

| No. | Components | Test Ex. 1-1 | Test Ex. 1-a | Test Ex. 1-b | Test Ex. 1-c | Test Ex. 1-d |
|---|---|---|---|---|---|---|
| | Average emulsion particle size of first oil phase | 614 nm | 690 nm | 3000 nm | 2800 nm | 611 nm |
| | Feeling in use (stickiness during application) | ○ | ○ | Δ | Δ | ○ |
| | Feeling in use (stickiness just after application) | ○ | Δ | ○ | Δ | Δ |
| | Emulsion stability (50° C. × 1M) | ○ | X | X | X | ○ |
| | Solubility stability (0° C. × 1M) | ○ | X | ○ | X | ○ |

*1 Silicone KF96A-6T: manufactured by Shin-Etsu Chemical Co., Ltd.
*2 APS-10-DMS: manufactured by Shin-Etsu Chemical Co., Ltd.
*3 PEMULEN TR-2: BF Goodrich (Production Method)
Production Method 1 (Emulsifying the First Oil Phase and the Second Oil Phase Separately):

The first oil phase is emulsified with, as an emulsifier, a POE/POP alkyl ether block polymer by a high-pressure emulsification method to obtain an O/W emulsion (the first emulsion). Separately, the second oil phase is emulsified with an alkyl-modified carboxyvinyl polymer to obtain an O/W emulsion (the second emulsion). Then both emulsions are mixed to obtain the aimed O/W emulsified composition.

Specifically, to a part of Component (1), Components (3) to (5) and Component (8) are added with heat, and the mixture is emulsified with a high-pressure emulsification device (manufactured by APV) to obtain the first emulsion (the emulsion particle size of the oil phase is 700 nm or less).

Components (11) and (12) are mixed, and the mixture is added to a solution in which Component (13) is dissolved in the rest of Component (1). The obtained mixture is then emulsified with a homomixer to obtain the second emulsion.

The first and second emulsions are mixed, and the other components are further added to and mixed with the mixture to obtain the aimed O/W emulsified composition (the first oil phase particle size ≦700 nm).

Production Method 1' (Emulsifying the First Oil Phase and the Second Oil Phase Separately):

The aimed O/W emulsified composition is obtained by using the same production method with Production method 1, except that the first emulsion is prepared by emulsifying the first oil phase with, as an emulsifier, a POE/POP alkyl ether block polymer by a microemulsification method using a hydrophilic solvent.

Specifically, Components (6), (7), (8), and a part of Component (1) are mixed, and a dissolved mixture of Components (3) to (5) is added thereto. The obtained mixture is emulsified with a homomixer to obtain the first emulsion (the emulsion particle size of the oil phase is 700 nm or less).

Components (11) and (12) are mixed, and the mixture is added to a solution in which Component (13) is dissolved in the rest of Component (1). The obtained mixture is then emulsified with a homomixer to obtain the second emulsion.

The first and second emulsions are mixed, and the other components are further added to and mixed with the mixture to obtain the aimed O/W emulsified composition (the first oil phase particle size ≦700 nm).

Production Method 2 (Emulsifying the First Oil Phase and the Second Oil Phase at Once):

The first oil phase in the preparation of the first emulsion in Production method 1' is replaced with a mixture of the first and second oil phases to obtain the aimed O/W emulsified composition.

Specifically, Components (6), (7), (8), and a part of Component (1) are mixed, and a dissolved mixture of Components (3) to (5) and a mixture of Components (11) and (12) are added thereto. The obtained mixture is emulsified with a homomixer, and the other components are added to and mixed with the emulsion to obtain the aimed O/W emulsified composition (the oil phase particle size ≦700 nm).

Production Method 3 (Emulsifying the First Oil Phase and the Second Oil Phase Separately):

The aimed O/W emulsified composition is obtained by using the same production method with Production method 1', except that the first and second oil phases are exchanged in each emulsification process.

Specifically, Components (6), (7), (8), and a part of Component (1) are mixed, and a dissolved mixture of Components (11) and (12) is added thereto. The obtained mixture is emulsified with a homomixer to obtain the second emulsion.

Components (3) to (5) are mixed, and then added to a solution in which Component (13) is dissolved in the rest of Component (1). The obtained mixture is then emulsified with a homomixer to obtain the first emulsion (the emulsion particle size of the oil phase is more than 700 nm).

The first and second emulsions are mixed, and the other components are added to and mixed with the mixture to obtain the aimed O/W emulsified composition (the first oil phase particle size >700 nm).

Production Method 4 (Emulsifying the First Oil Phase and the Second Oil Phase at Once):

The second oil phase in the preparation of the second emulsion in Production method 1' is replaced with a mixture of the first and second oil phases to obtain the aimed O/W emulsified composition.

Specifically, a dissolved mixture of Components (3) to (5) and Component (8) and a mixture of Components (11) and (12) are added to a solution in which Component (13) is dissolved in Component (1). The obtained mixture is then emulsified with a homomixer and the other components are added to and mixed with the emulsion to obtain the aimed O/W emulsified composition (the oil phase particle size >700 nm).

As shown in Table 1, when the first oil phase (organic UV absorber phase) and the second oil phase (silicone oil phase) are separately emulsified, and the average particle size of the first oil phase is 700 nm or less, the O/W emulsified composition with excellent formulation stability and feeling in use can be obtained (Test example 1-1). When the second oil phase (silicone oil phase) is not incorporated, a sticky feeling is caused just after application (Test example 1-d). Also even in a separate emulsification, when the emulsion particle size of the first oil phase exceeds 700 nm such as Test example 1-b, a sticky feeling is caused during application on skin, and the emulsion stability is not sufficient.

On the other hand, even in the same composition with Test example 1-1, when the first and second oil phases are mixed and then emulsified at once using POP/POE alkyl ether block polymer, the emulsified composition becomes unstable over time though the emulsion particle size of the oil phase can be 700 nm or less, as shown in Test example 1-a. In addition, the solid component which has been dissolved in the first oil phase (such as bis-ethylhexyloxyphenol methoxyphenyl triazine in Table 1) precipitates. Furthermore, in spite of the incorporation of silicone oil, stickiness is caused just after application. When the oil phases are emulsified at once with an alkyl-modified carboxyvinyl polymer, as shown in Test example 1-c, the emulsion particle size of the oil phase exceeds 700 nm, resulting in significantly deteriorated stability and feeling in use.

Example 2

Amount of Block Polymer

O/W emulsified compositions were prepared in the same method with Test example 1-1, except for changing the amounts of the block polymer POE(20)POP(80)cetyl ether as an emulsifier for the first oil phase.

TABLE 2

| Components | Test Ex. 1-1 | Test Ex. 2-a | Test Ex. 2-b |
|---|---|---|---|
| POE(20)POP(8)cetyl ether | 0.4 | 0.2 | 3.1 |
| Average emulsion particle size of first oil phase | 614 nm | 670 nm | 560 nm |
| Feeling in use (stickiness during application) | ◯ | ◯ | X |
| Feeling in use (stickiness just after application) | ◯ | ◯ | ◯ |
| Emulsion stability (50° C. × 1M) | ◯ | Δ | ◯ |
| Solubility stability (0° C. × 1M) | ◯ | ◯ | ◯ |

As shown in Table 2, when the amount of emulsifier for the first oil phase is too small, the emulsion stability tends to decrease. On the other hand, when the emulsifier is contained excessively, a sticky feeling is caused during application.

From these results, the amount of emulsifier for the first oil phase is preferably 0.3 to 3% by mass, more preferably 0.3 to 2% by mass, and particularly preferably 0.3 to 1% by mass, in the O/W emulsified composition of the present invention.

According to the present invention, as shown in Table 2, it is possible that a large amount of oil-soluble organic UV absorber (e.g., 8% by mass or more) is stably emulsified with use of an extremely small amount of emulsifier (e.g., 1% by mass or less) to provide an O/W emulsified composition excellent in UV protection ability, formulation stability, and feeling in use.

Example 3

Kind of Surfactant

O/W emulsified compositions were prepared in the same method with Test example 1-1, except for changing the kinds of block polymer POE(20)POP(80)cetyl ether as an emulsifier for the first oil phase.

TABLE 3

| Components | Test Ex. 1-1 | Test Ex. 3-1 | Test Ex. 3-2 | Test Ex. 3-a | Test Ex. 3-b | Test Ex. 3-c |
|---|---|---|---|---|---|---|
| POE(20)POP(8)cetyl ether [HLB = 12.5] | 0.4 | — | — | — | — | — |
| POE(50)POP(40)dimethyl ether [HLB = 17] | — | 0.4 | — | — | — | — |
| POE(35)POP(40)dimethyl ether [HLB = 12] | — | — | 0.4 | — | — | — |
| POE(30)behenyl ether [HLB = 18] | — | — | — | 0.4 | — | — |
| POE(60)glyceryl isostearate [HLB = 18.3] | — | — | — | — | 0.4 | — |
| POE(60)hydrogenated castor oil [HLB = 14.6] | — | — | — | — | — | 0.4 |
| POE(100)hydrogenated castor oil [HLB = 16.5] | — | — | — | — | — | — |
| POE(30)phytosterol [HLB = 18] | — | — | — | — | — | — |
| POE(30)cholestanol [HLB = 17] | — | — | — | — | — | — |
| POE(20)sorbitan monostearate [HLB = 14.9] | — | — | — | — | — | — |
| POE(20)sorbitan monolaurate [HLB = 16.9] | — | — | — | — | — | — |
| Average emulsion particle size of first oil phase | 614 nm | 604 nm | 690 nm | 1000 nm | 1500 nm | 2000 nm |
| Feeling in use (stickiness during application) | ◯ | ◯ | ◯ | Δ | Δ | Δ |
| Feeling in use (stickiness just after application) | ◯ | ◯ | ◯ | ◯ | ◯ | ◯ |
| Emulsion stability (50° C. × 1M) | ◯ | ◯ | ◯ | Δ | Δ | Δ |
| Solubility stability (0° C. × 1M) | ◯ | ◯ | ◯ | ◯ | ◯ | ◯ |

| Components | Test Ex. 3-d | Test Ex. 3-e | Test Ex. 3-f | Test Ex. 3-g | Test Ex. 3-h |
|---|---|---|---|---|---|
| POE(20)POP(8)cetyl ether [HLB = 12.5] | — | — | — | — | — |
| POE(50)POP(40)dimethyl ether [HLB = 17] | — | — | — | — | — |
| POE(35)POP(40)dimethyl ether [HLB = 12] | — | — | — | — | — |
| POE(30)behenyl ether [HLB = 18] | — | — | — | — | — |
| POE(60)glyceryl isostearate [HLB = 18.3] | — | — | — | — | — |
| POE(60)hydrogenated castor oil [HLB = 14.6] | — | — | — | — | — |
| POE(100)hydrogenated castor oil [HLB = 16.5] | 0.4 | — | — | — | — |
| POE(30)phytosterol [HLB = 18] | — | 0.4 | — | — | — |
| POE(30)cholestanol [HLB = 17] | — | — | 0.4 | — | — |
| POE(20)sorbitan monostearate [HLB = 14.9] | — | — | — | 0.4 | — |
| POE(20)sorbitan monolaurate [HLB = 16.9] | — | — | — | — | 0.4 |
| Average emulsion particle size of first oil phase | 1500 nm | 1000 nm | 1100 nm | 3100 nm | 3000 nm |
| Feeling in use (stickiness during application) | Δ | Δ | Δ | X | X |
| Feeling in use (stickiness just after application) | ◯ | ◯ | ◯ | ◯ | ◯ |

TABLE 3-continued

| Emulsion stability (50° C. × 1M) | Δ | Δ | Δ | X | X |
| Solubility stability (0° C. × 1M) | ○ | ○ | ○ | ○ | ○ |

As shown in Table 3, with the block polymer of the formula (1) or (2), the first oil phase could be easily emulsified to be 700 nm or less, and the O/W emulsified composition excellent in formulation stability and feeling in use could be obtained. However, with the other nonionic surfactants, even when the HLB was in the same range, it was difficult to obtain such an O/W emulsified composition.

Example 4

Amount of Organic UV Absorber

O/W emulsified compositions were prepared in the same method with Test example 1-1, except for changing the amounts of organic UV absorber.

TABLE 4

| Components | Test Ex. 4-a* | Test Ex. 4-b* | Test Ex. 4-c* | Test Ex. 4-d | Test Ex. 4-e | Test Ex. 4-f |
|---|---|---|---|---|---|---|
| Octocrylene | 11 | 5 | 5 | 0.5 | 4 | 5 |
| Ethylhexyl methoxycinnamate | 5 | 5 | 8 | 5 | 4 | 0.5 |
| Bis-ethylhexyloxyphenol methoxyphenyl triazine | 2 | 6 | 2 | 2 | 0.2 | 2 |
| Average emulsion particle size of first oil phase | 683 nm | 612 nm | 630 nm | 500 nm | 622 nm | 511 nm |
| Feeling in use (stickiness during application) | Δ | Δ | Δ | ○ | ○ | ○ |
| Feeling in use (stickiness just after application) | ○ | ○ | ○ | ○ | ○ | ○ |
| Emulsion stability (50° C. × 1M) | X | X | X | ○ | ○ | ○ |
| Solubility stability (0° C. × 1M) | ○ | X | ○ | X | ○ | X |
| UV protection ability | ◎ | ◎ | ◎ | X | X | X |

*Amount of POE(20)POP(8)cetyl ether is 1% by mass.

As shown in Test examples 4-a to 4-c, when octocrylene, ethylhexyl methoxycinnamate, or bis-ethylhexyloxyphenol methoxyphenyl triazine as an organic UV absorber is contained excessively, stickiness is caused or the emulsion stability decreases. In addition, when bis-ethylhexyloxyphenol methoxyphenyl triazine is contained excessively, precipitation over time may be caused.

From these results, in the O/W emulsified composition, it is preferred that the amount of octocrylene is 10% by mass or less, the amount of ethylhexyl methoxycinnamate is 7.5% by mass or less, and the amount of bis-ethylhexyloxyphenol methoxyphenyl triazine is 5% by mass or less.

In this context, as shown in Test examples 4-d to 4-f, when the amount of organic UV absorber is too small, the UV protection ability decreases. Thus, the total amount of organic UV absorbers is 8% by mass or more, more preferably 9% by mass or more, and particularly preferably 10% by mass or more, in the composition.

What is claimed is:

1. An oil-in-water emulsified composition, wherein (i) a first oil phase and (ii) a second oil phase are dispersed separately in an aqueous phase,
   (i) the first oil phase having average particle size of 700 nm or less, comprising an organic UV absorber, and being formed with, as an emulsifier, a polyoxyethylene/polyoxyalkylene alkyl ether block polymer that is present to an extent of 0.3 to 3% by mass in the oil-in-water emulsified composition and represented by formula (1) or (2):

$$R_1O-(PO)m-(EO)n-H \quad (1)$$

wherein $R_1$ is a hydrocarbon group having 16 to 18 carbon atoms; PO is an oxypropylene group, EO is an oxyethylene group, and PO and EO are added to each other in block form; and m and n respectively represent average addition mole numbers of PO and EO, 70>m>4, 70>n>10, and n>m; and $$R_2O-(AO)p-(EO)q-R_3 \quad (2)$$

wherein $R_2$ and $R_3$ are either identical to or different from one other, and each is a hydrocarbon group having 1 to 4 carbon atoms; AO is an oxyalkylene group having 3 to 4 carbon atoms, EO is an oxyethylene group, and AO and EO are added to each other in block form; and p and q respectively represent average addition mole number of AO and EO, $1 \leq p \leq 70$, $1 \leq q \leq 70$, and $0.2 < (q/(p+q)) < 0.8$, and wherein the first oil phase comprises, as the organic UV absorber,
octocrylene that is present to an extent of 1 to 10% by mass in the oil-in-water emulsified composition,
ethylhexyl methoxycinnamate that is present to an extent of 1 to 7.5% by mass in the oil-in-water emulsified composition, and
bis-ethylhexyloxyphenol methoxyphenyl triazine that is present to an extent of 0.5 to 5% by mass in the oil-in-water emulsified composition, and
(ii) the second oil phase comprising a silicone oil and being formed with, as an emulsifier, an alkyl-modified carboxyvinyl polymer.

2. The oil-in-water emulsified composition according to claim 1, wherein the organic UV absorber is present in the composition to an extent of 8% by mass or more.

3. A sunscreen cosmetic, consisting of the oil-in-water emulsified composition according to claim 1.

4. A sunscreen cosmetic, consisting of the oil-in-water emulsified composition according to claim 2.

5. A method for producing the oil-in-water emulsified composition according to claim 1, comprising:
emulsifying an aqueous phase and the first oil phase comprising the organic UV absorber with, as an emulsifier, the polyoxyethylene/polyoxyalkylene alkyl ether block polymer represented by the formula (1) or (2) to prepare a first oil-in-water emulsion, wherein the first oil phase with average particle size of 700 nm or less is dispersed in the aqueous phase;
emulsifying, separately from the first emulsion, an aqueous phase and the second oil phase comprising the silicone oil with, as an emulsifier, the alkyl-modified carboxyvinyl polymer to prepare a second oil-in-water emulsion, wherein the second oil phase is dispersed in the aqueous phase; and mixing the first and second emulsions to prepare the oil-in-water emulsified composition, wherein the first and second oil phases are separately dispersed in the aqueous phase.

6. A method for producing the oil-in-water emulsified composition according to claim 2, comprising:

emulsifying an aqueous phase and the first oil phase comprising the organic UV absorber with, as an emulsifier, the polyoxyethylene/polyoxyalkylene alkyl ether block polymer represented by the formula (1) or (2) to prepare a first oil-in-water emulsion, wherein the first oil phase with average particle size of 700 nm or less is dispersed in the aqueous phase;

emulsifying, separately from the first emulsion, an aqueous phase and the second oil phase comprising the silicone oil with, as an emulsifier, the alkyl-modified carboxyvinyl polymer to prepare a second oil-in-water emulsion, wherein the second oil phase is dispersed in the aqueous phase; and mixing the first and second emulsions to prepare the oil-in-water emulsified composition, wherein the first and second oil phases are separately dispersed in the aqueous phase.

7. A method for producing the oil-in-water emulsified composition according to claim 1, comprising:

emulsifying an aqueous phase and the first oil phase comprising the organic UV absorber with, as an emulsifier, the polyoxyethylene/polyoxyalkylene alkyl ether block polymer represented by the formula (1) or (2) to prepare a first oil-in-water emulsion, wherein the first oil phase with average particle size of 700 nm or less is dispersed in the aqueous phase; and emulsifying an aqueous phase, the second oil phase comprising the silicone oil, and the first emulsion with, as an emulsifier, the alkyl-modified carboxyvinyl polymer to prepare the oil-in-water emulsified composition, wherein the first and second oil phases are separately dispersed in the aqueous phase.

8. A method for producing the oil-in-water emulsified composition according to claim 2, comprising:

emulsifying an aqueous phase and the first oil phase comprising the organic UV absorber with, as an emulsifier, the polyoxyethylene/polyoxyalkylene alkyl ether block polymer represented by the formula (1) or (2) to prepare a first oil-in-water emulsion, wherein the first oil phase with average particle size of 700 nm or less is dispersed in the aqueous phase; and emulsifying an aqueous phase, the second oil phase comprising the silicone oil, and the first emulsion with, as an emulsifier, the alkyl-modified carboxyvinyl polymer to prepare the oil-in-water emulsified composition, wherein the first and second oil phases are separately dispersed in the aqueous phase.

* * * * *